(12) United States Patent
Schulz et al.

(10) Patent No.: US 9,468,440 B2
(45) Date of Patent: Oct. 18, 2016

(54) SURGICAL CLIP APPLICATOR

(71) Applicant: Aesculap AG, Tuttlingen (DE)

(72) Inventors: Peter Schulz, Loeffingen (DE); Pedro Morales, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 382 days.

(21) Appl. No.: 13/946,042

(22) Filed: Jul. 19, 2013

(65) Prior Publication Data

US 2014/0005696 A1 Jan. 2, 2014

Related U.S. Application Data

(63) Continuation of application No. PCT/EP2012/054106, filed on Mar. 9, 2012.

(30) Foreign Application Priority Data

Mar. 31, 2011 (DE) .......... 10 2011 001 706

(51) Int. Cl.
*A61B 17/10* (2006.01)
*A61B 17/128* (2006.01)
*A61B 17/08* (2006.01)
*A61B 17/00* (2006.01)
*A61B 17/29* (2006.01)

(52) U.S. Cl.
CPC .......... *A61B 17/105* (2013.01); *A61B 17/083* (2013.01); *A61B 17/1285* (2013.01); *A61B 2017/0046* (2013.01); *A61B 2017/0053* (2013.01); *A61B 2017/00477* (2013.01); *A61B 2017/2933* (2013.01)

(58) Field of Classification Search
None
See application file for complete search history.

(56) References Cited

U.S. PATENT DOCUMENTS

| 439,994 | A | 11/1890 | Ballard |
| 2,758,302 | A | 8/1956 | White |
| 2,988,314 | A | 6/1961 | Urich |

(Continued)

FOREIGN PATENT DOCUMENTS

| CA | 1 149 106 | 7/1983 |
| DE | 1 959 610 | 11/1972 |

(Continued)

OTHER PUBLICATIONS

Patent Abstracts of Japan, Abstract of Japanese Patent "Tissue Ligator", Publication No. 06-233774, Aug. 23, 1994, Japanese Application No. 05-022585, filed Feb. 10, 1993.

(Continued)

*Primary Examiner* — Tuan V Nguyen
(74) *Attorney, Agent, or Firm* — Lipsitz & McAllister, LLC

(57) ABSTRACT

To economically manufacture a surgical clip applicator for U-shaped or V-shaped clips, which allows secure closure of the clips when applied to tissue structures, in particular, also in the case of double-shank or multiple clips, it is proposed that the applicator comprise a handle portion, a shaft adjoining the handle portion, a clip applying tool arranged at the free end of the shaft, and a clip magazine, the applying tool comprising a mouthpiece with tool jaws for holding a clip during the application and a closing device for transferring the tool jaws from an open, idle position to a closed position, and the mouthpiece being made of a plastic material and being held separately from the closing device on the clip applicator.

15 Claims, 7 Drawing Sheets

(56) References Cited

U.S. PATENT DOCUMENTS

| | | |
|---|---|---|
| 3,270,745 A | 9/1966 | Wood |
| 3,317,973 A | 5/1967 | Finkle |
| 3,463,156 A | 8/1969 | McDermott |
| 3,616,497 A | 11/1971 | Esposito, Jr. |
| 3,629,912 A | 12/1971 | Klopp |
| 3,631,707 A | 1/1972 | Miller |
| 3,636,954 A | 1/1972 | Weston |
| 3,774,438 A * | 11/1973 | Weston ................ A61B 17/128 606/142 |
| 3,775,826 A | 12/1973 | Reed |
| 3,777,538 A | 12/1973 | Weatherly et al. |
| 3,856,016 A | 12/1974 | Davis |
| 3,916,908 A | 11/1975 | Leveen |
| 3,954,108 A | 5/1976 | Davis |
| 4,044,771 A | 8/1977 | Wannag |
| 4,152,920 A | 5/1979 | Green |
| 4,242,902 A | 1/1981 | Green |
| 4,296,751 A | 10/1981 | Blake, III et al. |
| 4,299,224 A | 11/1981 | Noiles |
| 4,388,747 A | 6/1983 | Plummer |
| 4,412,539 A | 11/1983 | Jarvik |
| 4,430,997 A | 2/1984 | DiGiovanni et al. |
| 4,444,181 A | 4/1984 | Wevers et al. |
| 4,449,531 A | 5/1984 | Cerwin et al. |
| 4,456,006 A | 6/1984 | Wevers et al. |
| 4,477,008 A | 10/1984 | Struble |
| 4,478,220 A | 10/1984 | Di Giovanni et al. |
| 4,509,518 A | 4/1985 | McGarry et al. |
| 4,512,345 A | 4/1985 | Green |
| 4,514,885 A | 5/1985 | Delahousse et al. |
| 4,527,726 A | 7/1985 | Assell et al. |
| 4,549,544 A | 10/1985 | Favaron |
| 4,576,165 A | 3/1986 | Green et al. |
| 4,586,503 A | 5/1986 | Kirsch et al. |
| 4,602,632 A | 7/1986 | Jorgensen |
| 4,637,395 A | 1/1987 | Caspar et al. |
| 4,646,740 A | 3/1987 | Peters et al. |
| 4,648,542 A | 3/1987 | Fox et al. |
| 4,733,664 A | 3/1988 | Kirsch et al. |
| 4,854,317 A | 8/1989 | Braun |
| 4,887,601 A | 12/1989 | Richards |
| 4,929,240 A | 5/1990 | Kirsch et al. |
| 4,983,176 A | 1/1991 | Cushmann et al. |
| 5,032,127 A | 7/1991 | Frazee et al. |
| 5,047,038 A | 9/1991 | Peters et al. |
| 5,084,057 A | 1/1992 | Green et al. |
| 5,112,343 A | 5/1992 | Thornton |
| 5,160,339 A | 11/1992 | Chen et al. |
| 5,171,247 A | 12/1992 | Hughett et al. |
| 5,171,250 A | 12/1992 | Yoon |
| 5,207,692 A | 5/1993 | Kraus et al. |
| 5,217,473 A | 6/1993 | Yoon |
| 5,222,961 A | 6/1993 | Nakao et al. |
| 5,236,440 A | 8/1993 | Hlavacek |
| 5,282,807 A | 2/1994 | Knoepfler |
| 5,366,459 A | 11/1994 | Yoon |
| 5,397,046 A | 3/1995 | Savage et al. |
| 5,431,668 A | 7/1995 | Burbank, III et al. |
| 5,441,509 A | 8/1995 | Vidal et al. |
| 5,452,500 A | 9/1995 | Revis |
| 5,464,413 A | 11/1995 | Siska, Jr. et al. |
| 5,472,132 A | 12/1995 | Savage et al. |
| 5,527,318 A | 6/1996 | McGarry |
| 5,527,320 A | 6/1996 | Carruthers et al. |
| D371,390 S | 7/1996 | Johnson |
| 5,542,949 A | 8/1996 | Yoon |
| 5,584,425 A | 12/1996 | Savage et al. |
| 5,591,178 A | 1/1997 | Green et al. |
| 5,607,436 A | 3/1997 | Pratt et al. |
| 5,609,599 A | 3/1997 | Levin |
| 5,625,931 A | 5/1997 | Visser et al. |
| 5,626,585 A | 5/1997 | Mittelstadt et al. |
| 5,626,586 A | 5/1997 | Pistl et al. |
| RE35,525 E | 6/1997 | Stefanchik et al. |
| 5,643,291 A | 7/1997 | Pier et al. |
| 5,665,097 A | 9/1997 | Baker et al. |
| 5,681,330 A | 10/1997 | Hughett et al. |
| 5,700,271 A | 12/1997 | Whitfield et al. |
| 5,725,542 A | 3/1998 | Yoon |
| 5,752,973 A | 5/1998 | Kieturakis |
| 5,772,673 A | 6/1998 | Cuny et al. |
| 5,779,720 A | 7/1998 | Walder-Utz et al. |
| 5,788,716 A | 8/1998 | Kobren et al. |
| D401,626 S | 11/1998 | Shyu |
| 5,843,097 A | 12/1998 | Mayenberger et al. |
| 5,893,506 A | 4/1999 | Powell |
| 5,894,979 A | 4/1999 | Powell |
| 5,895,394 A | 4/1999 | Kienzle et al. |
| 6,015,417 A | 1/2000 | Reynolds, Jr. |
| RE36,720 E | 5/2000 | Green et al. |
| 6,210,419 B1 | 4/2001 | Mayenberger et al. |
| 6,258,105 B1 | 7/2001 | Hart et al. |
| 6,261,303 B1 | 7/2001 | Mayenberger et al. |
| 6,273,898 B1 | 8/2001 | Kienzle et al. |
| 6,352,541 B1 | 3/2002 | Kienzle et al. |
| 6,428,548 B1 | 8/2002 | Durgin et al. |
| 6,599,298 B1 | 7/2003 | Forster et al. |
| 6,837,895 B2 | 1/2005 | Mayenberger |
| 7,207,997 B2 | 4/2007 | Shipp et al. |
| 7,572,266 B2 | 8/2009 | Young et al. |
| D600,749 S | 9/2009 | Azman et al. |
| D600,750 S | 9/2009 | Azman et al. |
| 7,678,125 B2 | 3/2010 | Shipp |
| 8,506,580 B2 | 8/2013 | Zergiebel et al. |
| 8,512,357 B2 | 8/2013 | Viola |
| 2002/0099388 A1 | 7/2002 | Mayenberger |
| 2004/0044363 A1 | 3/2004 | Fowler |
| 2004/0147942 A1 | 7/2004 | Chao |
| 2004/0153100 A1 | 8/2004 | Ahlberg et al. |
| 2005/0119677 A1 | 6/2005 | Shipp |
| 2005/0149063 A1 | 7/2005 | Young et al. |
| 2005/0177177 A1 | 8/2005 | Viola |
| 2005/0234478 A1* | 10/2005 | Wixey ................ A61B 17/12 606/142 |
| 2005/0256529 A1 | 11/2005 | Yawata et al. |
| 2006/0212049 A1 | 9/2006 | Mohiuddin |
| 2007/0073314 A1* | 3/2007 | Gadberry ............ A61B 17/128 606/142 |
| 2008/0045981 A1 | 2/2008 | Margolin et al. |
| 2008/0103510 A1* | 5/2008 | Taylor ................ A61B 17/08 606/143 |
| 2008/0188872 A1 | 8/2008 | Duff |
| 2008/0312670 A1 | 12/2008 | Lutze et al. |
| 2010/0137886 A1 | 6/2010 | Zergiebel et al. |
| 2010/0274262 A1 | 10/2010 | Schulz et al. |
| 2013/0150870 A1 | 6/2013 | Morales |
| 2013/0289583 A1 | 10/2013 | Zergiebel et al. |

FOREIGN PATENT DOCUMENTS

| | | |
|---|---|---|
| DE | 2 245 405 | 3/1973 |
| DE | 24 05 390 | 8/1975 |
| DE | 28 45 213 | 4/1979 |
| DE | 30 21 099 | 12/1980 |
| DE | 30 14 578 | 11/1981 |
| DE | 34 04 561 | 8/1984 |
| DE | 33 35 986 | 4/1985 |
| DE | 34 43 367 | 6/1985 |
| DE | 37 04 760 | 3/1988 |
| DE | 43 03 544 | 9/1993 |
| DE | 94 06 926 | 9/1994 |
| DE | 44 29 084 | 6/1995 |
| DE | 690 28 200 | 2/1997 |
| DE | 691 22 002 | 2/1997 |
| DE | 196 03 889 | 8/1997 |
| DE | 695 25 083 | 8/2002 |
| DE | 696 34 391 | 1/2006 |
| DE | 20 2006 000 329 | 4/2006 |
| DE | 20 2006 011 054 | 10/2006 |
| DE | 10 2006 001 344 | 7/2007 |
| DE | 20 2007 003 398 | 7/2007 |
| DE | 696 36 965 | 12/2007 |
| DE | 20 2009 006 1 | 8/2009 |
| DE | 20 2011 000 754 | 6/2011 |

(56) References Cited

FOREIGN PATENT DOCUMENTS

| | | |
|---|---|---|
| DE | 20 2011 000 755 | 7/2011 |
| EP | 0 406 724 | 1/1991 |
| EP | 0 409 569 | 1/1991 |
| EP | 0 283 526 | 2/1991 |
| EP | 0 567 965 | 11/1993 |
| EP | 0 621 006 | 10/1994 |
| EP | 0 793 944 | 9/1999 |
| EP | 0 697 198 | 5/2002 |
| EP | 1 198 204 | 2/2003 |
| GB | 2 073 022 | 10/1981 |
| JP | H05208019 | 8/1993 |
| JP | 2005522259 | 7/2005 |
| JP | 2010523282 | 7/2010 |
| WO | WO 95/23557 | 9/1995 |
| WO | WO 96/16602 | 6/1996 |
| WO | WO 96/32891 | 10/1996 |
| WO | WO 98/18389 | 5/1998 |
| WO | WO 99/27859 | 6/1999 |
| WO | WO 00/42922 | 7/2000 |
| WO | WO 2007/009099 | 1/2007 |

OTHER PUBLICATIONS

Leaflet of Aesculap AG & Co. KG "Titanium Ligature Clips and Applicators", 8 pages, Feb. 2002.
Brochure of Aesculap AG & Co. KG "Challenger Ti", 12 pages, Feb. 2002.
U.S. Appl. No. 60/117,079, filed Jan. 25, 1999, Johnson et al.

* cited by examiner

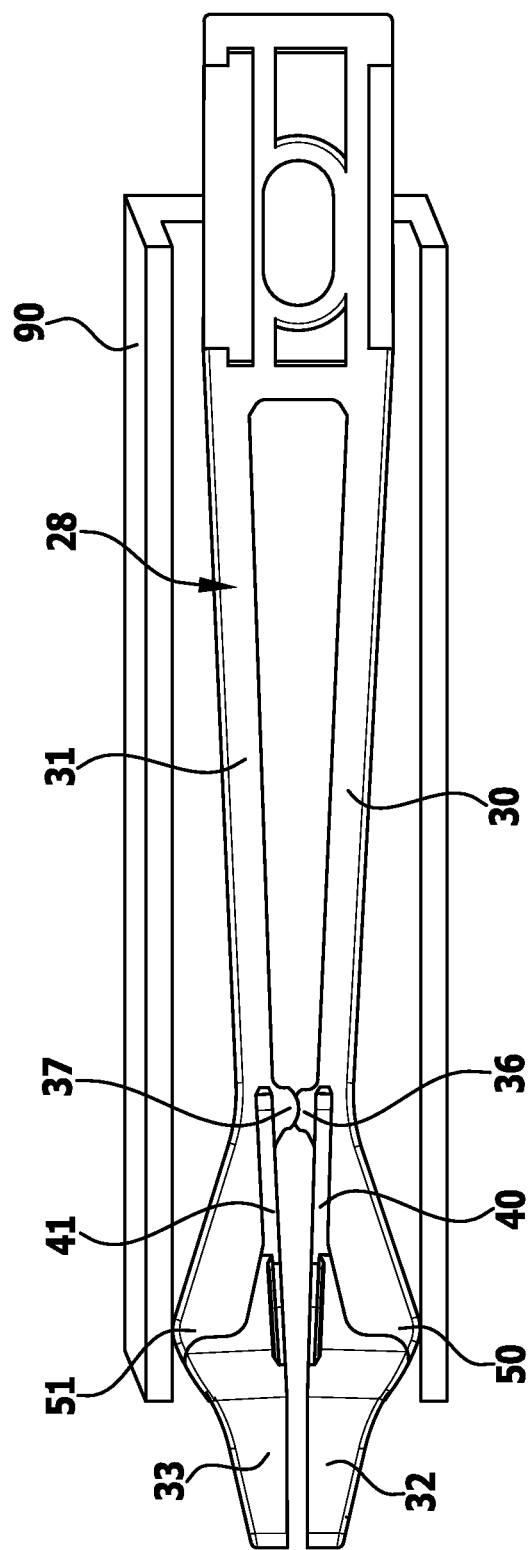

SURGICAL CLIP APPLICATOR

This application is a continuation of international application number PCT/EP2012/054106 filed on Mar. 9, 2012 and claims the benefit of German application number 10 2011 001 706.2 filed on Mar. 31, 2011, which are incorporated herein by reference in their entirety and for all purposes.

BACKGROUND OF THE INVENTION

The invention relates to a surgical clip applicator with which generally U-shaped or V-shaped clips are typically applied to tissue structures of a patient, for example, a blood vessel, and then closed.

The surgical clip applicator comprises a handle portion, a shaft adjoining the handle portion, a clip applying tool arranged at the free end of the shaft, and a clip magazine in which a plurality of U-shaped or V-shaped clips are stored, which can be fed singly to the clip applying tool.

The applying tool comprises a mouthpiece with tool jaws for holding a clip during the application and a closing device for transferring the tool jaws from an open, idle position to a closed position in which the clips are closed and then adhere to the tissue structure or the blood vessel and occlude it.

The clip magazine is often held exchangeably on the clip applicator, as is known, for example, from DE 196 03 889 A1. A clip applicator with exchangeable clip magazine is disclosed therein. Herein the handle portion with the applicator shaft and the clip applying tool is used several times, whereas the clip magazine is used only once and is disposed of after depletion of the supply of clips. Following sterilization, the rest of the applicator can be fitted again with a fresh clip magazine and used again.

Owing to the harsh sterilization conditions, deformations may occur to some extent in clip guide tracks on which the clips are fed to the clip applying tool singly and/or in the applying tool, as a result of which, for example, clips become jammed or clips fall out of the applicator before they are fed to the applying tool. The clip applicator then has to be repaired. It is then no longer possible to put the clip magazine in use at that point in time with its supply of clips to further use.

In EP 0 793 944 B1 a clip applicator is described in which not only the clip magazine but also the mouthpiece can be exchanged as required. The problem with this applicator is that the need to exchange the mouthpiece can only be recognized by applying a clip as a test or possibly only during an operation on the patient. In such a case, the clip applicator has to be repaired, which means that the clip magazine with the remaining clips has to be discarded and the mouthpiece then exchanged, and the instrument sterilized and fitted with a new clip magazine before it can be used again.

In accordance with US 2005/0256529 A1 an applicator with a reusable handle portion and a disposable clip magazine exchangeably connectable to the handle portion is proposed, in which the steel mouthpiece is exchanged together with the clip magazine. Here the mouthpiece is exchanged each time with the used magazine, and a new mouthpiece is supplied along with each clip magazine, so that the problems occurring in usage, as described above, are prevented. However, the manufacturing costs of such disposable clip magazines with steel mouthpieces are relatively high.

A further alternative is described in U.S. Pat. No. 4,296,751, in which the complete applicator is designed as disposable article. For cost reasons it is also proposed therein that the forceps jaws of the mouthpiece be made of plastic material or plastic material reinforced with metal.

A disadvantage of this embodiment is that the plastic material, even when reinforced with plastic, does not produce satisfactory results when closing the clips, as the closing forces to be applied can only be transmitted to an insufficient extent by the plastic forceps jaws. Double-shank or multiple clips cannot be used with such applicators as the necessary closing forces cannot be transmitted here.

The object of the present invention is to propose a clip applicator, which, on the one hand, can be manufactured economically and, on the other hand, allows secure closure of the clips when applied to tissue structures, in particular, also in the case of double-shank or multiple clips.

SUMMARY OF THE INVENTION

This object is accomplished in accordance with the invention by a surgical clip applicator having the features of claim 1.

Owing to the mouthpiece being produced from a plastic material, cost-effective manufacture of the parts of the clips applicator to be used only once is possible. On the other hand, the components of higher quality, in particular, those made of steel, such as the handle portion and the closing device, are reusable and thus contribute further to the cost-effectiveness of the surgical clip applicator in accordance with the invention.

In addition, owing to the separate manufacture of the mouthpiece, the plastic material can be specially designed and selected for the specific demands, so that it can then take into account the mechanical requirements arising, in particular, from the closing of the clips and the expenditure of force necessary therefor.

In this connection, the plastic materials are selected, in particular, from polyolefins, polycarbonate, polyamide, polyetheretherketone, polyphenylene sulfide, polyether imide and liquid crystal polymers.

These polymers may then be fiber-reinforced, in particular, glass fiber-reinforced, with the proportion of fiber ranging, in particular, from approximately 20 to approximately 60% by weight, further preferred approximately 30 to approximately 50% by weight.

In particular, such plastic mouthpieces can be injection-molded and are, therefore, most cost-effective to produce. These are suitable not only for closing so-called single-leg clips, but also double-shank clips, where the deformation forces which have to be applied in order to securely close the clip are almost double.

It has proven particularly expedient to form the mouthpiece in the shape of a fork with two substantially parallel arms, which carry, at the free ends, tool jaws which, in particular, are also integrally formed on these and, in particular, are shaped by injection molding.

Also, fork-shaped mouthpieces have the further advantage that the mouthpiece opens again elastically and brings the tool jaws into the open, idle position without further structural elements having to assist this. This reduces the number of parts for manufacture of the clip applicator in accordance with the invention and, therefore, also the manufacturing costs.

A particularly preferred embodiment of the surgical clip applicator comprises a mouthpiece in which the tool jaws are held for pivotal movement on the mouthpiece arms. For this purpose, the mouthpiece arms then comprise, in their regions adjacent to the tool jaws, bearing elements which can be brought into abutment with each other and which in abutment with each other form a pivot bearing for the tool jaws. The bearing elements are arranged on the mouthpiece arms on surfaces facing each other and are preferably of self-centering construction.

In a further preferred embodiment of the invention, the mouthpiece arms are provided with protuberances on their outer surfaces located opposite the tool jaws. These protuberances reinforce the sections of the tool jaws and allow safe application of the closing forces to the clips to be applied.

In addition, these protuberances enable implementation of a simple closing mechanism, in which the closing device comprises a slide, which grips around the fork-shaped mouthpiece and is displaceable parallel to the longitudinal direction of the mouthpiece from a first, proximal position to a second, distal position. The protuberances of the mouthpiece arms are then configured as guides with which the distal end of the slide engages and, when displaced into the second position, transfers the tool jaws to their closed position.

This feature results, in particular, in connection with the use of bearing elements in the area of transition from the mouthpiece arms to the tool jaws in a mechanically very simple and efficient design, which, in addition, makes do with small component thicknesses and, therefore, a minimal expenditure of material.

Preferred bearing elements are of complementary construction, so that a centering results when they abut against each other. In particular, the bearing elements are constructed as plug and socket.

In view of the exchangeability of the mouthpiece, it is preferred if it is held on the clip magazine and is exchangeable together with it. The clip magazine can, therefore, be assembled together with the mouthpiece and packed ready for use, so that exchange of clip magazine and mouthpiece can be carried out in one operation and involve no more expenditure than the mere exchange of a clip magazine.

In such a case, the tool, not yet discussed in detail, for singling the clips and feeding them to the mouthpiece of the applying tool is then preferably also exchanged together with these.

In a further embodiment of the invention, the clip magazine is configured with the shaft and the closing device of the applying tool as a constructional unit, which is connectable to the handle portion so as to be separable and exchangeable in one step, so that only the mechanical parts of the handle portion are reusable and need be subjected to sterilization conditions.

For secure holding of the clips, the tool jaws preferably comprise a receiving area in which the clip to be applied is received after it has been fed singly to the applying tool.

The receiving area for the clip to be applied comprises, in each case, an abutment surface for one of the legs of the clip, with the abutment surface extending at least over part of the length of the legs and, therefore, guiding these.

A clip applicator in accordance with the invention preferably comprises receiving areas in which the abutment surface for the legs is followed by a recess in which a connecting region of the legs or an apex of the clip is received when the tool jaws are in the closed position.

This has the advantage that the receiving area widens at this point and, therefore, the clips to be applied do not have to be fully compressed at the apex in order to arrive at the required dimension of the closing gap between the legs, which is typically 0.25 mm or less, in particular, 0.07 mm to approximately 0.15 mm.

On the one hand, by avoiding excessive forces for compressing the apex of the clip to be applied, the expenditure of force is reduced for the operating surgeon who must apply it in order to close a clip. On the other hand, the stress on the mouthpieces made of plastic material is also reduced, so that, in turn, the design and also the choice of material with regard to the plastic material can be optimized here, with a saving of material.

The abutment surfaces in the area of the free ends of the legs of the clips are preferably provided with a setback, so that the physical contact between the legs of the clip and the tool jaws remains limited to the necessary area that is required for closing the clips. Owing to the U-shape or V-shape of the clips, it is sufficient for these to have contact with the tool jaws in the middle section of the legs, as a pretension with respect to their free ends is already achieved during the closing on account of the clip shape.

The abutment surfaces are preferably of such dimensions that when the tool jaws are in the closed position, the legs abut only with a middle section against the tool jaws, however, the legs abut against the tool jaws, in particular, over approximately one third of their length, in particular, half of their length or somewhat more, when the tool jaws are in the closed position.

Furthermore, the recesses of the receiving areas of the tool jaws have a depth perpendicular to the closing direction of the clip legs, which corresponds approximately to half of the thickness of a clip leg or its diameter or more. In particular, the depth of the recess is approximately equal to the thickness or diameter of the leg of the clip.

The thickness of a clip leg is to be understood as its extent in the direction of the closing direction of the clip.

Approximately twice the diameter or thickness of a clip leg or more is preferably chosen for the length of the recess, which receives the connecting region of the clip legs, parallel to the longitudinal direction of the clip leg.

Further preferred, approximately four times the diameter or thickness of a clip leg or less is chosen for the length of the recess.

It is thus ensured that the clip, also under load, is securely fixed in its position between the tool jaws of the clip applicator.

In a further preferred embodiment of the clip applicator in accordance with the invention, the abutment surfaces are provided with a guide element, which ensures alignment of the clips to be applied in the tool jaws.

In simple or one-leg clips, this guide element is often configured as a groove. In so-called double-shank clips, the guide element may comprise a projection which between the parallel legs comes to rest on one side of the clip and thus ensures orientation and guidance of the double-shank clip. This applies accordingly in the case of clips with, for example, three parallel legs.

These and further advantages of the invention will be explained in further detail hereinbelow with reference to the drawings.

BRIEF DESCRIPTION OF THE DRAWINGS

FIGS. 6A and 6B show a schematic representation of the mouthpiece of FIG. 4 in the idle position and the closed position.

DETAILED DESCRIPTION OF THE INVENTION

Figure 1:
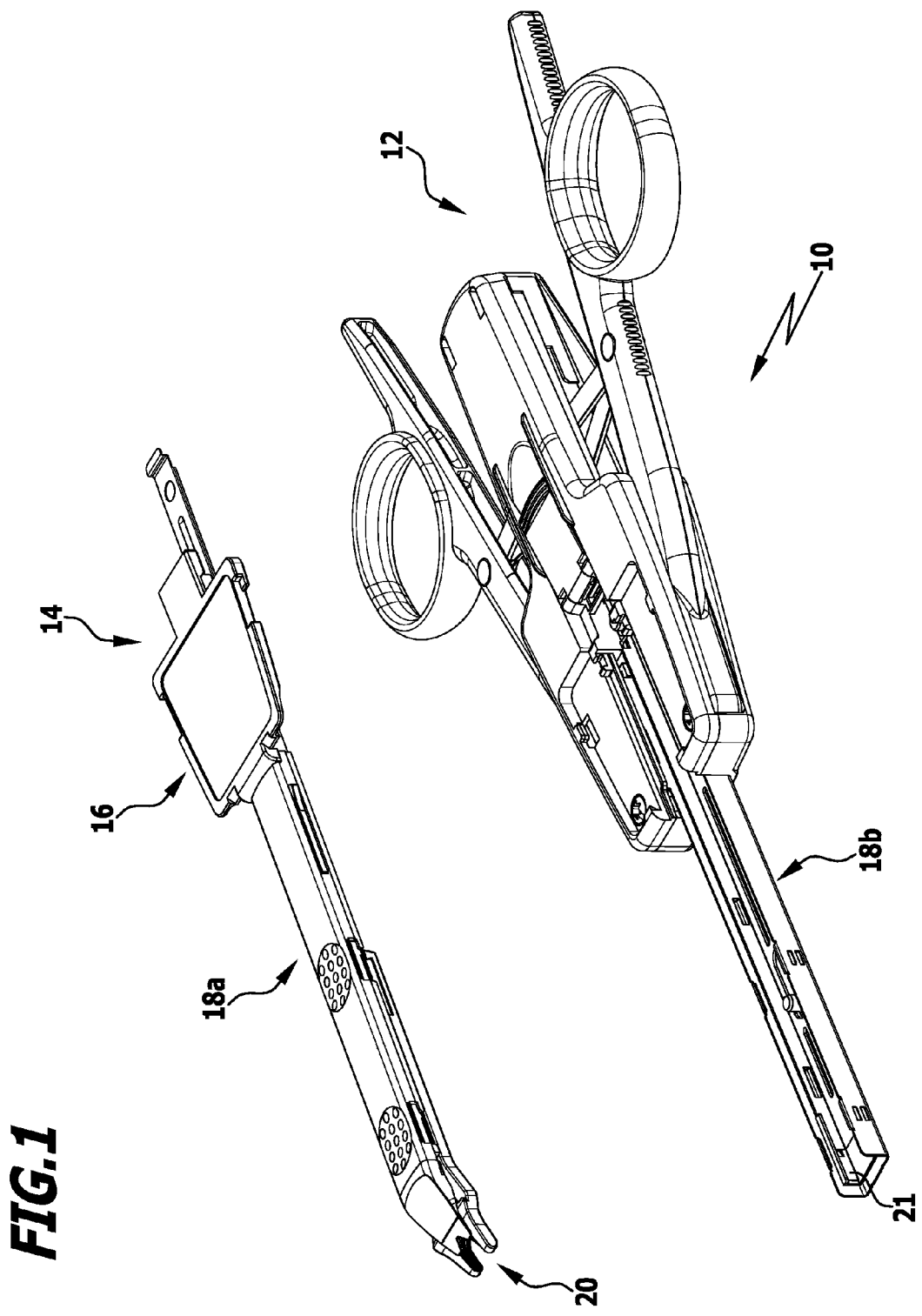
FIG. 1 shows a clip applicator in accordance with the invention.

FIG. 1 shows a clip applicator 10 in accordance with the invention with a handle portion 12 and a clip magazine 14 separated from the handle portion 12. The clip magazine 14 is releasably connectable in a latching manner to the handle portion 12, so that it can be easily replaced by a new magazine when the supply of clips stored in the magazine is used up.

The clip magazine 14 comprises next to a mounting and holding device 16 with which the clip magazine 14 is attachable to the handle 12, a shaft part 18a and at the free end thereof a mouthpiece 20 as part of the clip applying tool of the applicator.

The handle portion contains a part of the shaft 18b integrated therein, in which a closing device 21 is accommodated as part of the applying tool of the applicator 10. Here the closing device 21 is formed as a slide, the distal end of which engages partially around the mouthpiece 20 in the assembled state.

Figure 2:
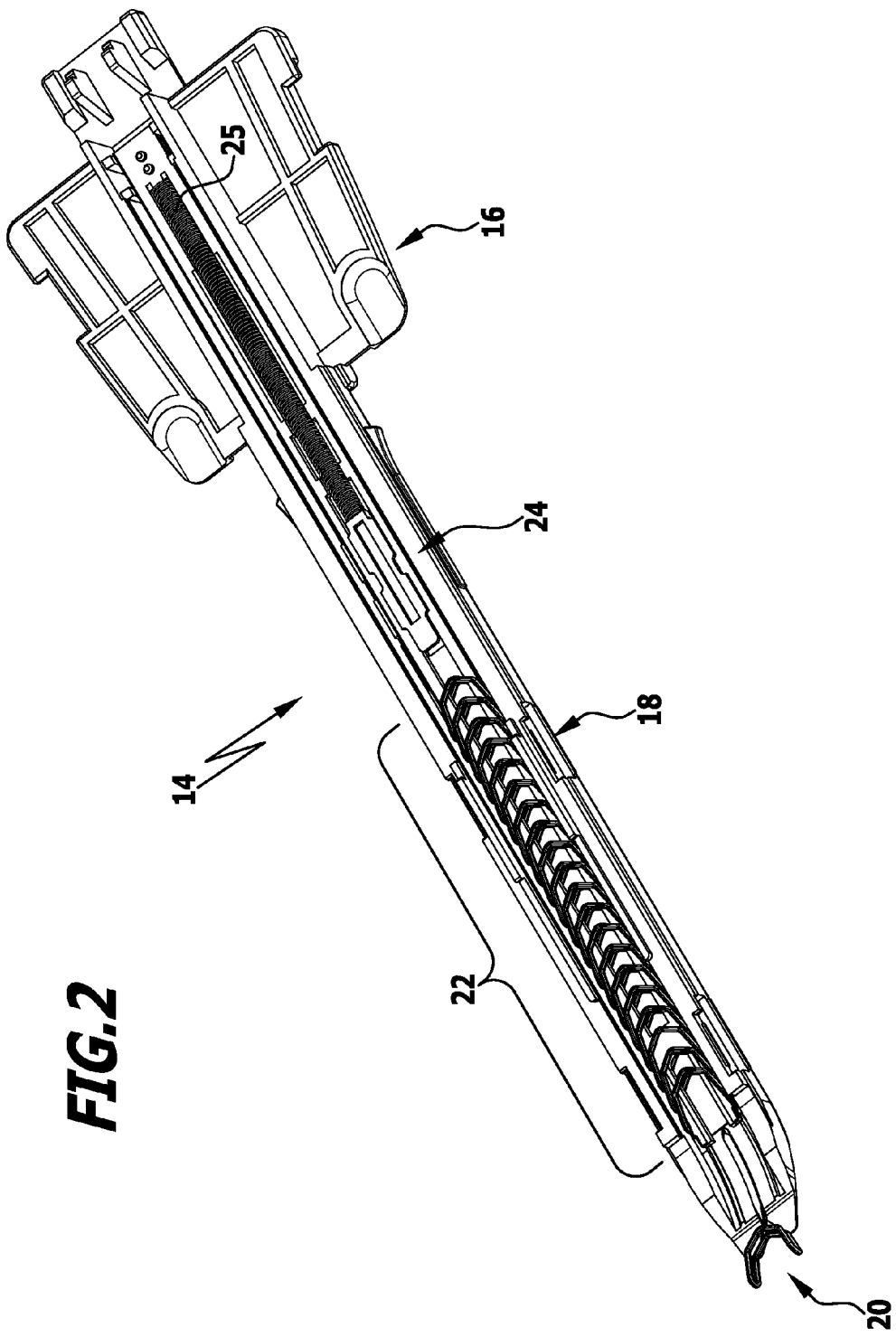
FIG. 2 shows the clip magazine, separated from the handle portion, of the clip applicator from FIG. 1 from below in a partially disassembled state.

In FIG. 2 the clip magazine 14 is shown from below in a partially disassembled state, so that the supply of clips 22 arranged in the clip magazine 14 or its shaft part 18 is visible.

Also visible in FIG. 2 is an advancing mechanism 24, with which, aided by the helical spring 25, the clips can be fed singly from the supply of clips 22 to the applying tool 20.

Figure 3:
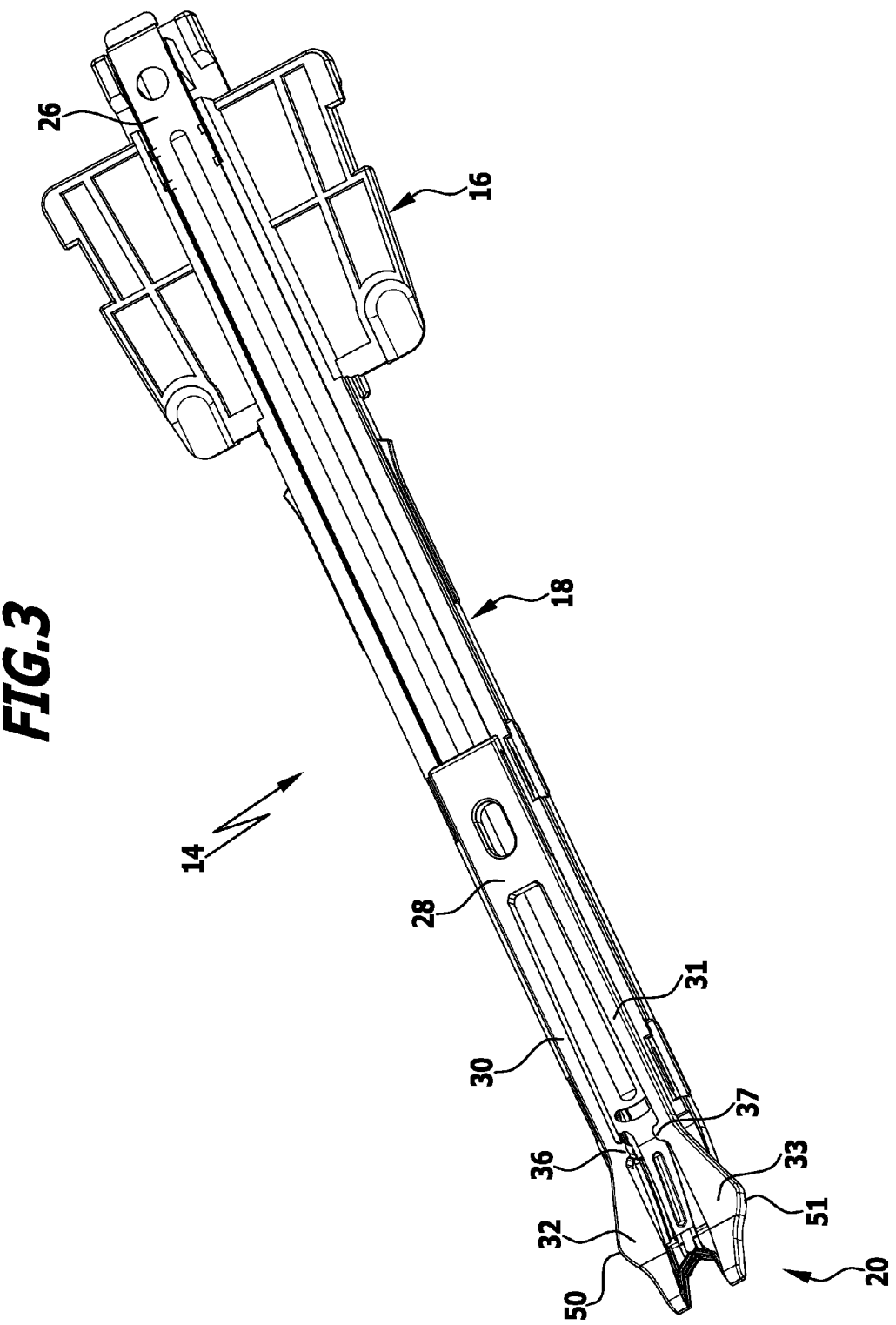
FIG. 3 shows the clip magazine from FIG. 2 completed and with the mouthpiece mounted.
Figure 4:
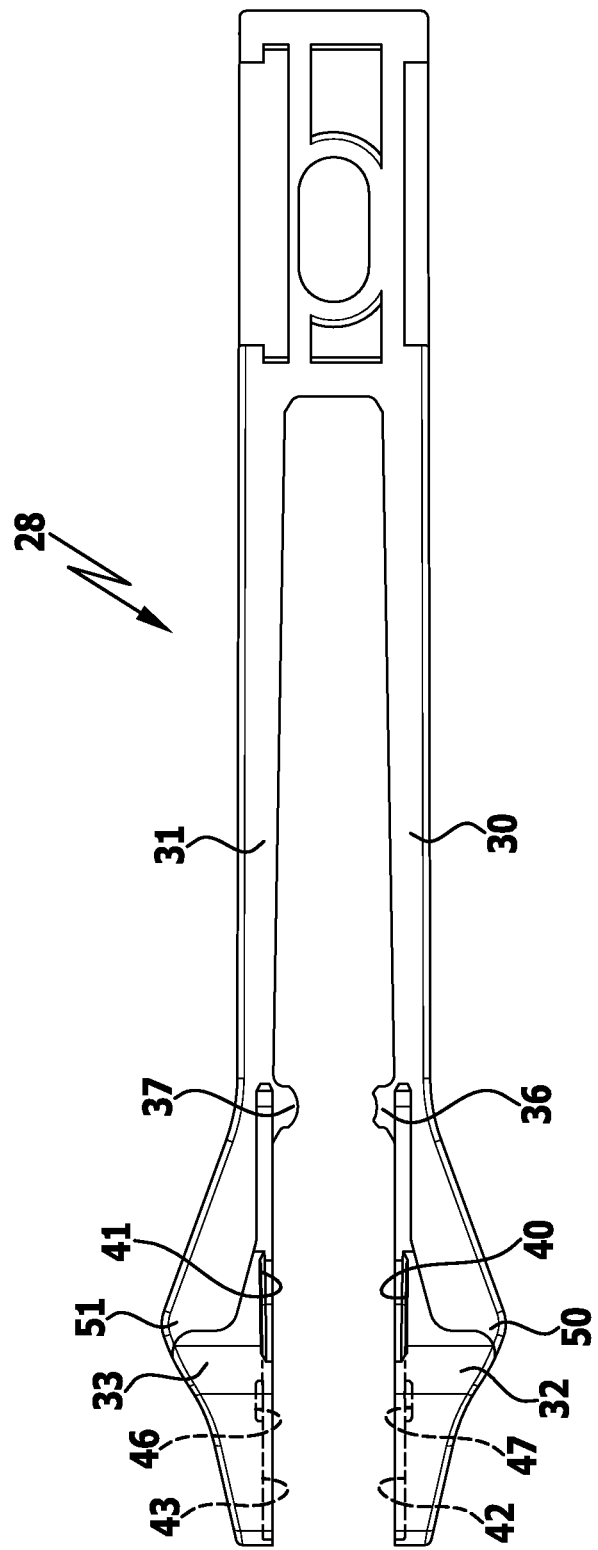
FIG. 4 shows the mouthpiece from FIG. 3.

In FIG. 3, the magazine 14 is also provided with a feeder tongue 26 and, finally, the mouthpiece 28, shown again in detail in FIG. 4, is clipped on from below.

The mouthpiece 28 is of fork-shaped configuration and comprises two parallel arms 30, 31, on the free ends of which tool jaws 32, 33 are integrally formed. At the area of transition between the arms 30, 31 and the tool jaws 32 and 33, respectively, the arms 30, 31 comprise bearing elements 36, 37, which project towards each other in the shape of plugs into the space between the two arms 30, 31.

The bearing elements 36, 37 are of complementary configuration. In the example of FIGS. 3 and 4, the bearing element 36 is of concave configuration at its free inwardly extending end, whereas the bearing element 37 is of corresponding convex configuration at its free end.

When the tool jaws 32, 33 are brought closer together from their open, idle position shown in FIGS. 3 and 4 into a closed position, the bearing elements 36, 37 engage each other and center the tool jaws 32, 33 in the correct alignment in relation to each other. When the closing force on the tool jaws 32, 33 is increased, these are then brought closer together in a pivotal movement with their free ends until they reach the final closed position, with the bearing elements 36, 37 defining the pivot axis of the pivotal movement.

On the upper side shown in FIG. 4, the mouthpiece 28 comprises in the proximal area of the tool jaws 32, 33 upwardly open guides 40, 41, which receive an advanced clip with its free legs.

The guides 40, 41 continue to the free (distal) end of the tool jaws 30, 33 as grooves 42, 43, in which a clip is held in its end position until it is applied.

As indicated by broken lines in FIG. 4, at their proximal end the grooves 42, 43 comprise recesses 46, 47 in which connecting regions or apexes of the clips to be applied can engage with the bulge formed there when the clip is closed. It is thus possible to close the clips during the application without fully compressing the area adjacent to the apex of the clip to the gap dimension required for the legs of the clip. The expenditure of force for closing the clips is thereby reduced, so that the load on the mouthpiece made of plastic material is further minimized.

For implementation of a simple closing mechanism, the tool jaws 32, 33 are provided on their outer sides with protuberances 50, 51, via which closure of the tool jaws 32, 33 can be brought about by translational movements of a slide (not shown in FIG. 4).

Figure 5:
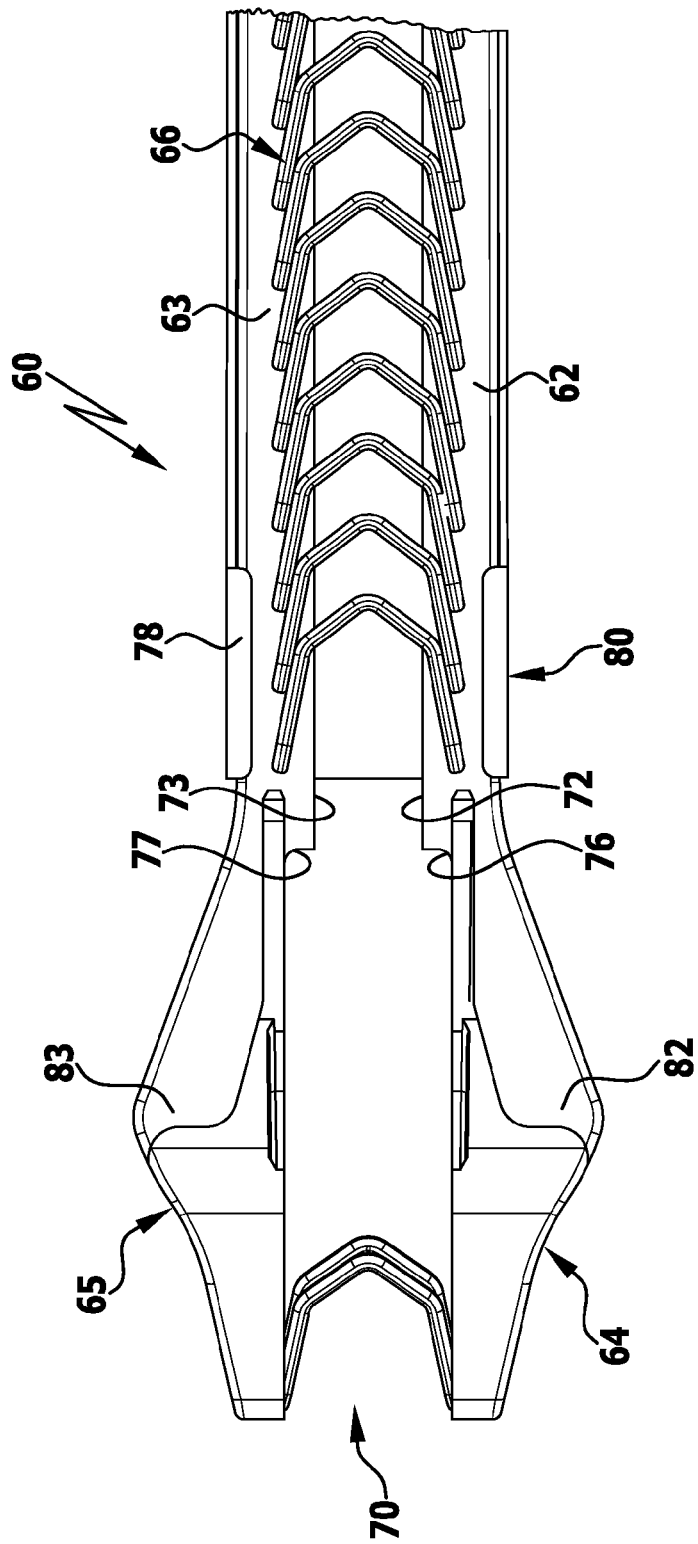
FIG. 5 shows an alternative mouthpiece of a clip applicator in accordance with the invention, held on a clip magazine.

FIG. 5 shows an alternative embodiment of a mouthpiece 60 of a clip applicator in accordance with the invention. The mouthpiece 60 is again of fork-shaped construction with arms 62, 63, on the free ends of which tool jaws 64, 65 are integrally formed. In FIG. 5, the mouthpiece 60 is shown with a supply of clips 66 and a double-shank clip 70 held singly in the tool jaws 64, 65.

The embodiment of the mouthpiece 60 has a bearing element construction which is different from that of the mouthpiece 28. Here the bearing elements are formed by simple flat abutment surfaces 72, 73, and an articulated connection of the jaws 64, 65 with the arms 62, 63 is achieved by the arms being formed with a setback 76, 77 on the inner side of the fork-shaped mouthpiece. A slide 78, which grips around the arms 62, 63 with its distal end area 80, is actuated in order to actuate the mouthpiece 60 or the tool jaws 64, 65 for application and closure of the clip 70. When the slide 78 is pushed out of its first position shown in FIG. 5 in the direction towards the free end of the tool jaws 64, 65, the tool jaws 64, 65 are pivoted about the pivot axes formed by the setbacks 76, 77, with the protuberances 82, 83 of the tool jaws 64, 65 serving as guide for the transmission of force.

Figure 6A:
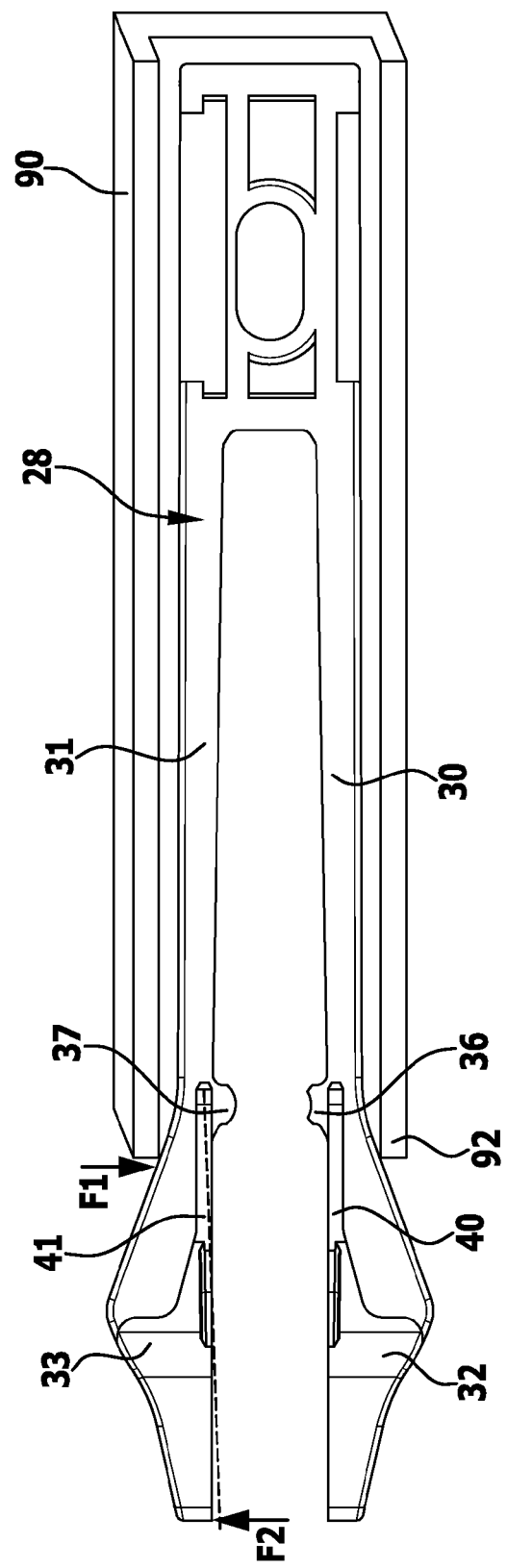

This closure mechanism is shown again in greater detail in a schematic representation of the mouthpiece 28 and a slide 90 in FIGS. 6A and 6B.

FIG. 6A shows the mouthpiece 28 in the open, idle position of the tool jaws 32, 33, with the slide 90 of the associated closure mechanism remaining in its first proximal position.

The distal end 92 of the slide 90 is located at the area of transition of the arms 30, 31 to the jaws 32, 33, in which the bearing elements 36, 37 are also arranged. In this position, a clip (not shown) can be pushed via the guides 40, 41 into its end position between the tool jaws 32, 33.

To apply the clip, the slide 90 is moved out of its proximal position into a distal position shown in FIG. 6B, with the distal end 92 sliding along the protuberances 50, 51 and thereby bringing the tool jaws 32, 33 closer to each other until the bearing elements 36, 37 enter into contact with each other. The force F1 exerted by the slide is counteracted by the force F2, which comes from the resistance caused by the clip during the closing.

A further translational movement of the slide 90 to the distal position then causes a pivoting of the tool jaws 32, 33 about the pivot bearing formed by the bearing elements 36, 37. The end position which the slide 90 finally reaches is shown in FIG. 6B, in which the tool jaws 32, 33 remain in a closed position, in which the distal ends of the tool jaws are aligned substantially parallel to each other, and the clip (not shown in FIG. 6B) is applied to a tissue structure of a patient, for example, a blood vessel.

The invention claimed is:

1. Surgical clip applicator for generally U-shaped or V-shaped clips, comprising:
   a handle portion,
   a shaft adjoining the handle portion,
   a clip applying tool arranged at a free end of the shaft, and
   a clip magazine,
   the clip applying tool comprising a mouthpiece with tool jaws for holding a clip during application of the clip and a closing device for transferring the tool jaws from an open, idle position to a closed position,
   the mouthpiece being made of a plastic material and being held separately from the closing device on the clip applicator;
   wherein:
   the mouthpiece is of a fork-shaped configuration with two substantially parallel arms and carries, at free ends of the two substantially parallel arms, the tool jaws which are integrally formed on the two substantially parallel arms;
   the tool jaws are held for pivotal movement towards one another on the two substantially parallel arms, the two substantially parallel arms comprising two bearing elements which project towards each other and which are adapted to be brought into abutment when the tool jaws are transferred from the open, idle position to the closed position, and
   the two bearing elements forming a pivot bearing for imparting the pivotal movement to the tool jaws when the two bearing elements are brought in abutment with each other by the closing device.

2. Clip applicator in accordance with claim 1, wherein the plastic material is a fiber-reinforced plastic material, a proportion of fiber being approximately 20 to approximately 60% by weight.

3. Clip applicator in accordance with claim 1, wherein the plastic material is selected from polyolefin, polycarbonate, polyamide, polyetheretherketone, polyphenylene sulfide, polyether imide and liquid crystal polymers.

4. Clip applicator in accordance with claim 1, wherein the two substantially parallel arms each comprise a protuberance on an outer surface of each of the two substantially parallel arms, which protuberances are located opposite the tool jaws.

5. Clip applicator in accordance with claim 4, wherein the closing device comprises a slide, which engages the fork-shaped mouthpiece and is displaceable parallel to a longitudinal direction of the mouthpiece from a first, proximal position to a second, distal position, and the protuberances of the two substantially parallel arms are configured as guides with which a distal end of the slide engages and, when displaced into the second position, transfers the tool jaws to the closed position.

6. Clip applicator in accordance with claim 1, wherein:
   the mouthpiece is held on the clip magazine; and
   the mouthpiece and the clip magazine are removeably coupled to the handle portion.

7. Clip applicator in accordance with claim 1, wherein the clip magazine forms with the shaft and clip applying tool a unit which is separable from the handle portion and removeably coupled to the handle portion.

8. Clip applicator in accordance with claim 1, wherein the tool jaws each comprise a receiving area for a clip to be applied.

9. Clip applicator in accordance with claim 8, wherein:
   the clip comprises legs;
   the receiving areas for the clip to be applied each comprise an abutment surface for one of the legs, which extends at least over part of a length of the legs, and a recess in which a connecting region of the legs of the clip is arranged when the tool jaws are in the closed position.

10. Clip applicator in accordance with claim 9, wherein the recess has a depth perpendicular to a closing direction of the clip legs, which corresponds approximately to a diameter or thickness of the clip leg or more.

11. Clip applicator in accordance with claim 10, wherein a length of the recess parallel to a longitudinal direction of the clip leg corresponds approximately to twice the diameter or thickness of the clip leg or more.

12. Clip applicator in accordance with claim 11, wherein the length of the recess corresponds approximately to four times the diameter or thickness of the clip leg or less.

13. Clip applicator in accordance with claim 9, wherein the abutment surfaces comprise a guide element.

14. Clip applicator in accordance with claim 13, wherein the guide element comprises a groove.

15. Clip applicator in accordance with claim 13, wherein the guide element comprises a projection.

* * * * *